United States Patent [19]
Nishiyama et al.

[11] Patent Number: 6,121,250
[45] Date of Patent: Sep. 19, 2000

[54] LAVAGE SOLUTION FOR INTESTINAL TRACT

[75] Inventors: Kaname Nishiyama; Chie Murase; Nobuyo Kawanaka, all of Osaka, Japan

[73] Assignee: Nissho Corporation, Osaka-fu, Japan

[21] Appl. No.: 09/148,492

[22] Filed: Sep. 4, 1998

[30] Foreign Application Priority Data

Sep. 5, 1997 [JP] Japan ................................. 9-240538

[51] Int. Cl.$^7$ ..................... A61K 31/715; A61K 31/695; C07C 31/18
[52] U.S. Cl. ................. 514/57; 514/54; 514/58; 514/60; 514/63; 568/852
[58] Field of Search ................. 514/54, 60, 57, 514/63; 568/852

[56] References Cited

U.S. PATENT DOCUMENTS

| | | | |
|---|---|---|---|
| 4,800,087 | 1/1989 | Mehta | 424/497 |
| 5,124,144 | 6/1992 | Giorgetti et al. | 424/78.01 |
| 5,274,001 | 12/1993 | Borody | 514/474 |

FOREIGN PATENT DOCUMENTS

| | | |
|---|---|---|
| 892787 | 3/1962 | United Kingdom . |
| 1128922 | 10/1968 | United Kingdom . |
| WO 86/06633 | 11/1986 | WIPO . |
| WO 87/00754 | 2/1987 | WIPO . |

OTHER PUBLICATIONS

G. P. Gorelashvili et al.; "X–ray contrast agents for the large intestine containing siloxanes and gum arabic and barium sulfate"; Chemical Abstracts; vol. 110, No. 13, p. 364, column 2, Abstract No. 131477y; Mar. 27, 1989.

G. R. Davis et al.; "Development of a lavage solution associated with minimal water and electrolyte absorption or secretion"; Chemical Abstracts; vol. 93, No. 6, p. 460, column 1, Abstract No. 53919h; Aug. 11, 1980.

G. Davis et al; Inhibition of Water and Electrolyte Absorption by Polyethylene Glycol (PEG); Gastroenterology; 79, pp. 35–39; 1980.

J. Ernstoff et al; "A Randomized Blinded Clinical Trial of a Rapid Colonic Lavage Solution (Golytely) Compared With Standard Preparation for Colonoscopy and Barium Enema"; Gastroenterology; 84, pp. 1512–1516; 1983.

G. Davis et al; "Development of a Lavage Solution Associated with Minimal Water and Electrolyte Absorption or Secretion"; Gastroenterology; 78, pp. 991–995; 1980.

*Primary Examiner*—Gary L. Kunz
*Assistant Examiner*—Everett White
*Attorney, Agent, or Firm*—Kubovcik & Kubovcik

[57] ABSTRACT

A lavage solution for intestinal tract which is easily applied in a treatment conducted prior to endoscopy of the intestines, surgery of the intestines and the like and hardly generates foam upon actual use and is stable as a pharmaceutical preparation is disclosed. The lavage solution for intestinal tract is an emulsified liquid mainly consisting of water-soluble high-molecular compound and electrolyte and an antifoaming agent of a silicone type.

14 Claims, 3 Drawing Sheets

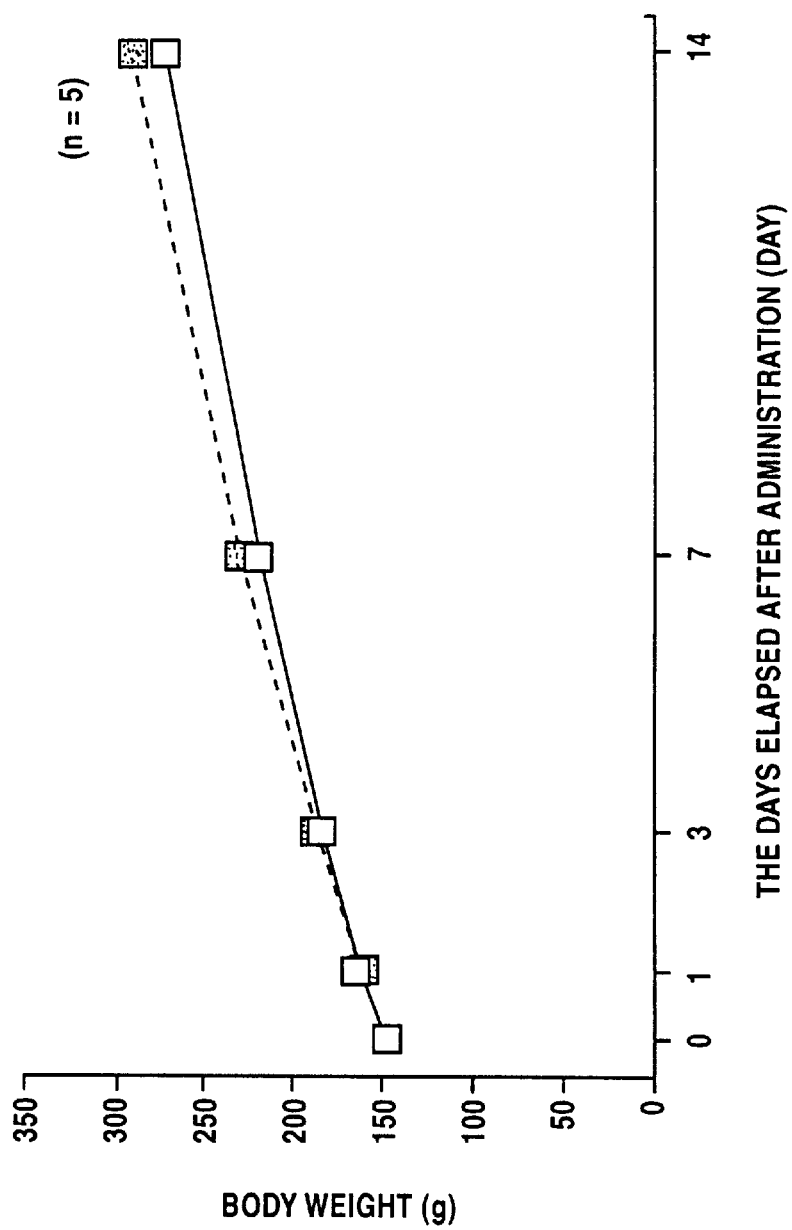

LAVAGE SOLUTION FOR INTESTINAL TRACT

FIELD OF THE INVENTION

The present invention relates to a lavage solution for the intestinal tract which is used for washout of the contents of the intestinal tract in a treatment conducted prior to endoscopy, surgery of the intestines or the like.

BACKGROUND OF THE INVENTION

With regard to lavage solutions for the intestinal tract, examples of known ones are a combination of polyethylene glycol or mannitol with an electrolyte [Gastroenterology, 78, 991 (1980)], a combination of polyethylene glycol and xylose with an electrolyte [Gasteroenterology, 79, 35 (1980)], a combination of polyethylene glycol with an electrolyte [Gastroenterology, 84, 1512 (1981) and Japanese Laid-Open Patent Publications Sho-63/500523 (PCT), Hei-01/125319, Hei-01/132527 and Hei-02/292223], a combination of at least one water-soluble high-molecular weight compound selected from polyethylene glycol, dextran, dextrin, hydroxyetliyl starch, polydextrose, gum arabic and pectin with an electrolyte (Japanese Laid-Open Patent Publication Hei-03/284620), a combination of erythritol and/or xylitol with an electrolyte (Japanese Laid-Open Patent Publication Hei-03/284620), a combination of fructo-oligosaccharide with an electrolyte (Japanese Laid-Open Patent Publication Hei-03/291228), and a combination of at least one compound selected from lactitol, maltitol and carboxymethyl cellulose with an electrolyte (Japanese Laid-Open Patent Publication Hei-05/255092).

However, such a lavage solution for the intestinal tract which is in a liquid form of a composition for cleaning the intestinal tract is very viscous and, therefore, foam is apt to be generated in the intestines upon its application or administration and, in addition, the generated foam hardly disappears therein. Accordingly, such solution has a disadvantage that satisfactory observation in the test or operation is disturbed or, due to its adhesion onto a lens of a camera, precise diagnosis is not possible. In view of the above, it is necessary in actual clinical practice to administer an antifoaming agent to a patient prior to a clinical test or surgery for removing the foam which is generated by the use of the lavage solution.

The present inventors tried to develop a lavage solution for the intestinal tract wherein an antifoaming agent is added to a conventional lavage solution for the intestinal tract in order to solve the above-mentioned difficulties in practical use. However, there was a problem that the liquid phase was separated into an aqueous phase and oily phase whereby the effect of the antifoaming agent was not achieved.

An object of the present invention is to provide a lavage solution for the intestinal tract that is more easily applicable, hardly generates foam in practical use and is stable as a pharmaceutical preparation.

SUMMARY OF THE INVENTION

The present inventors conducted an intensive study for solving the above-mentioned problems and found that, when an Si-containing antifoaming agent is previously diffused in a mixed powder of a water-soluble high-molecular weight compound and electrolyte, the powder is easily emulsified and dispersed upon dissolution into water and said emulsified state can be maintained.

Thus, the present invention relates to a lavage solution for the intestinal tract (hereinafter simply referred to as "lavage solution") which is characterized in that an emulsified liquid agent mainly consisting of water-soluble high-molecular weight compound and electrolyte contains an Si-containing antifoaming agent.

BRIEF DESCRIPTION OF THE DRAWINGS

FIG. 3 is a graph showing the changes in body weight of rats described in the Acute Toxicity Test Example.

DESCRIPTION OF PREFERRED EMBODIMENTS

Figure 1:
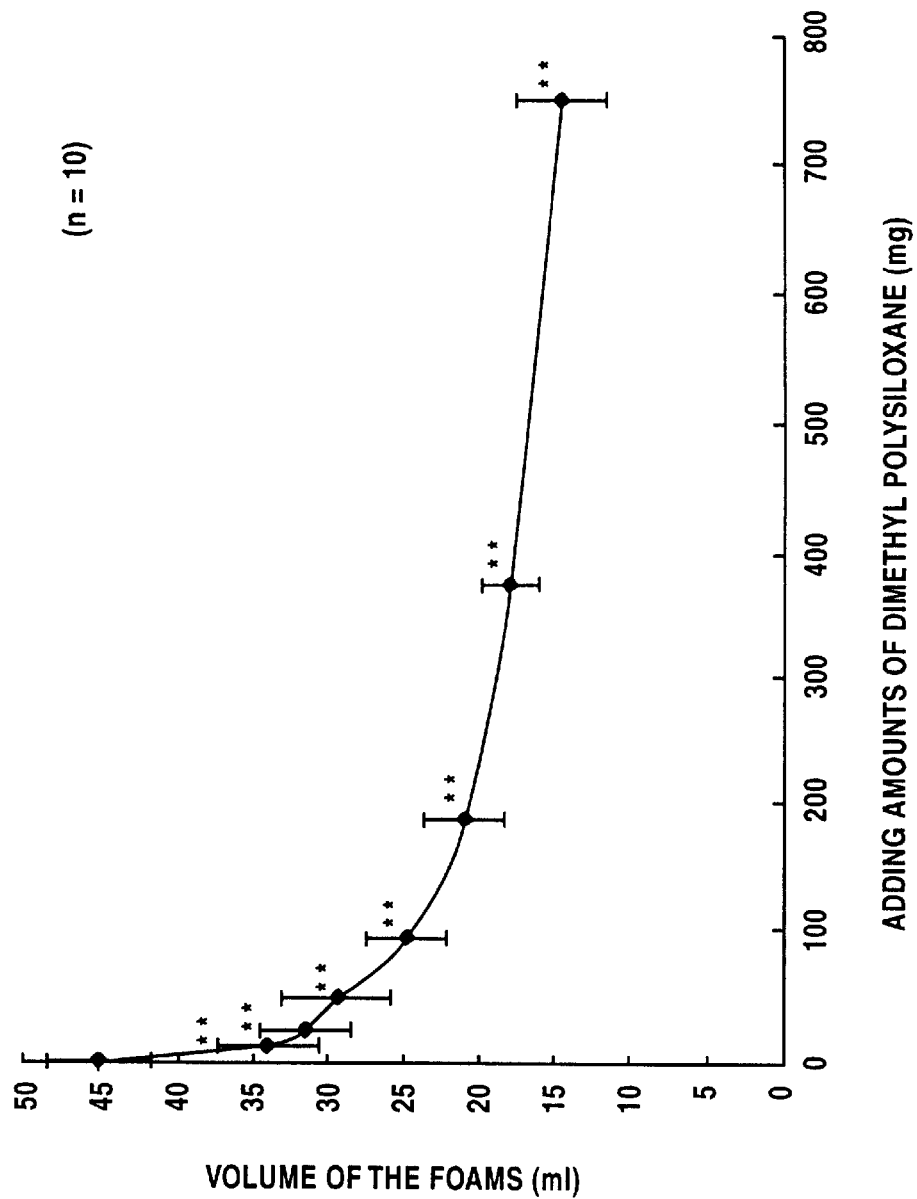
FIG. 1 is a graph showing the volume changes in the foam generated on a liquid surface in the antifoaming test described in Test Example 1 using sodium lauryl sulfate.

Appropriate examples of the water-soluble high-molecular weight compound which is one of the main components of the lavage solution according to the present invention are polyethylene glycol, dextran, dextrin, hydroxyethyl starch, polydextrose, gum arabic, pullulan, pectin and carboxymethyl cellulose. Polyethylene glycol is particularly preferred.

The electrolyte which is another main component of the lavage solution according to the present invention can be any electrolyte that is suitable for administration to humans. Examples of the electrolyte are sodium sulfate, potassium chloride, sodium chloride and sodium bicarbonate.

As a result of the addition of an Si-containing antifoaming agent, the lavage solution according to the present invention hardly generates foam. The Si-containing antifoaming agent used in the present invention is a so-called silicone-type antifoairing agent that is known as a pharmaceutical additive or as a food additive and can be appropriately selected from silicone resin and silicone oil. Among them, dimethyl polysiloxane is particularly preferred. It is preferred that the antifoaming agent is contained in the lavage solution in an amount of 0.2–400 mg/liter.

In the lavage solution according to the present invention, it is preferred that the amounts of water-soluble high-molecular weight compound and the ions of the electrolyte are selected from the following compositional ranges.

| | |
|---|---|
| Water-soluble high-molecular weight compound | 10–160 g/liter |
| $Na^+$ | 30–150 mEq/liter |
| $K^+$ | 3–20 mEq/liter |
| $Cl^-$ | 20–70 mEq/liter |
| $HCO_3^-$ | 10–30 mEq/liter |
| $SO_4^{2-}$ | 0–100 mEq/liter |

Incidentally, the lavage solution according to the present invention may be appropriately compounded with sweeteners such as sodium salt of saccharine, perfumes such as fruit essence and the like for improving the drinkability thereof.

The lavage solution according to the present invention may be prepared, for example, in a liquid form as follows. The Si-containing antifoaming agent is added to the water-soluble high-molecular weight compound and the electrolyte in an amount within the above-mentioned ranges, and mixed well with an amount of water which is sufficient to make a total volume of, for example, one liter together with other additives, if necessary.

It is also possible to use the lavage solution according to the present invention by dissolving a dosage form such as a powder, granules and fine granules upon practical use.

In order to illustrate the present invention, methods of preparing the lavage solution according to the present invention will be described in the following examples. Then a test example for showing the effects and an acute toxicity test example of the lavage solution according to the present invention will be described as well.

EXAMPLE 1

Dimethyl polysiloxane (14 mg) was added to a powdery composition consisting of 118 g of polyethylene glycol 4000 powder (polyethylene glycol powder having a molecular weight of 4000), 2.93 g of sodium chloride, 1.485 g of potassium chloride, 3.37 g of sodium bicarbonate and 11.37 g of sodium sulfate and the composition was well mixed to prepare a cleaning composition for the intestinal tract in the form of a powder. Then said cleaning composition for the intestinal tract in powder form was placed in a two-liter bottle, an appropriate amount of water was added thereto, the mixture was well shaken to dissolve the composition completely and additional water was added to make a total volume of two liters whereupon an emulsified liquid agent (i.e., lavage solution according to the present invention) for one administration was prepared.

EXAMPLE 2

Dimethyl polysiloxane (14 mg) was added to 118 g of polyethylene glycol 4000 powder and the composition was well mixed. Then, to the mixture were added 2.93 g of sodium chloride, 1.485 g of potassium chloride, 3.37 g of sodium bicarbonate and 11.37 g of sodium sulfate to prepare a cleaning composition for the intestinal tract in powder form. This cleaning composition for the intestinal tract in powder form was subjected to the same treatment as in Example 1 to prepare an emulsified liquid agent for one administration.

EXAMPLE 3

Dimethyl polysiloxane (14 mg) was added to a powdery composition consisting of 2.93 g of sodium chloride, 1.485 g of potassium chloride, 3.37 g of sodium bicarbonate and 11.37 g of sodium sulfate and the mixture was mixed well. Then 118 g of polyethylene glycol 4000 powder was added thereto to prepare a cleaning composition for the intestinal tract in powder form. This cleaning composition for the intestinal tract in powder form was subjected to the same treatment as in Example 1 to prepare an emulsified liquid agent for one administration.

Comparative Example 1

A powdery composition consisting of 118 g of polyethylene glycol 4000 powder, 2.93 g of sodium chloride, 1.485 g of potassium chloride, 3.37 g of sodium bicarbonate and 11.37 g of sodium sulfate was placed in a two-liter bottle, an appropriate amount of water was added thereto followed by shaking so that the powdery composition was completely dissolved therein and additional water was added thereto to make a total volume of two liters. To this solution was added 14 mg of dimethyl polysiloxane followed by mixing by means of shaking. However, it was not easy to prepare a stable emulsified liquid agent in which dimethyl polysiloxane was dispersed.

Test Example 1
Antifoaming Test Using Sodium Lauryl Sulfate

Each of 40 ml of an emulsified liquid agent of a cleaning composition for the intestinal tract prepared in the same manner as in Example 1 (amount of dimethyl polysiloxane added: 10, 25, 50, 95, 190, 380 and 750 mg) or a commercially available lavage solution for the intestinal tract (prepared by dissolving a powdery composition consisting of 118 g of polyethylene glycol 4000 powder, 2.93 g of sodium chloride, 1.485 g of potassium chloride, 3.37 g of sodium bicarbonate and 11.37 g of sodium sulfate in water to make two liters; i.e., a comparative solution) was charged in a 100-ml measuring cylinder equipped with a ground stopper. To each of these reagents was added 10 ml of a foaming medium containing 0.25 w/v % of hydroxyethyl cellulose and 0.01 w/v % of sodium lauryl sulfate. The measuring cylinder was stoppered and shaken 20 times to generate foam. The measuring cylinder was allowed to stand for 15 seconds and the volume of the foam that remained on the liquid surface was measured. The test was repeated 10 times with each solution. The results are shown in FIG. 1. It will be apparent from FIG. 1 that the lavage solution according to the present invention significantly reduced the generation of foam as compared with the comparative solution. In FIG. 1, the plots are average values and the mark means **"$p<0.01$" as compared with the comparative group.

Test Example 2

Antifoaming Test Using Serum Albumin

Figure 2:
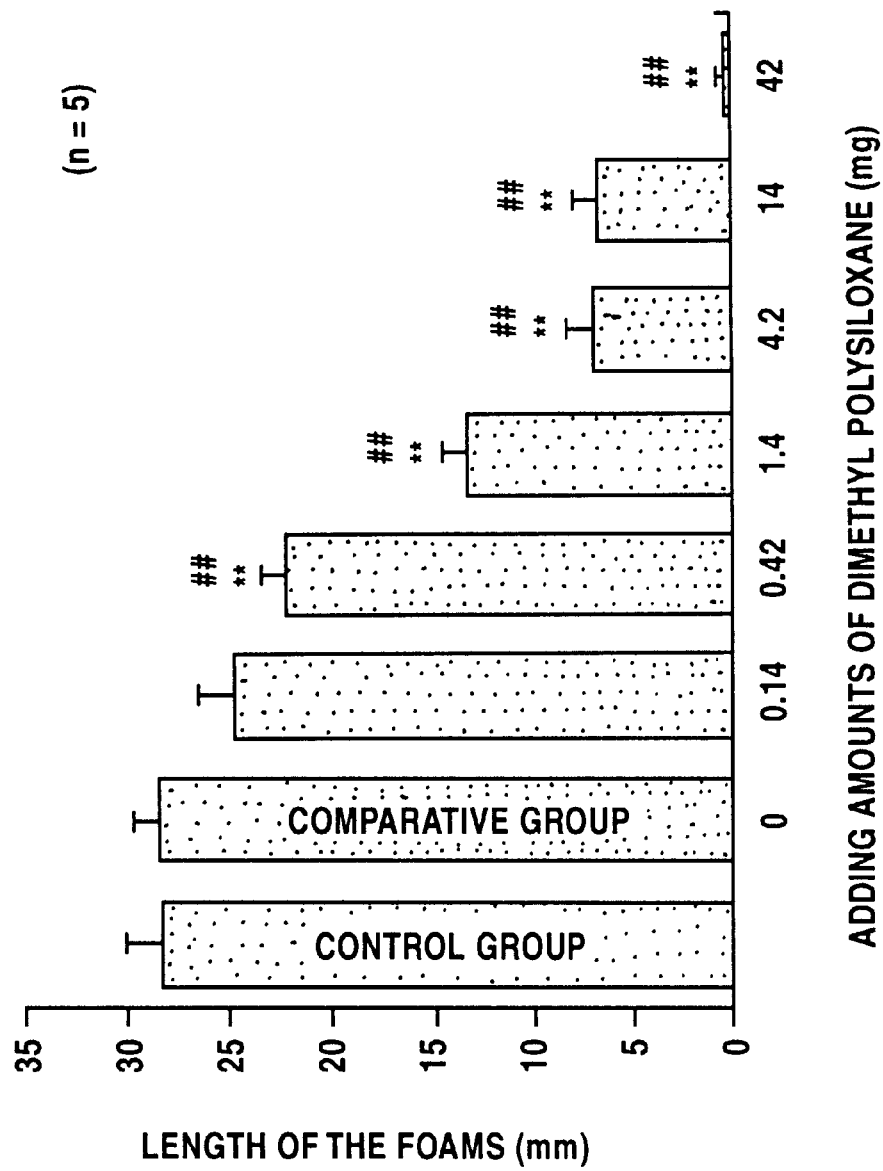
FIG. 2 is a graph showing the length of foam generated on a liquid surface in the antifoaming test described in Test Example 2 using serum albumin.

Each of 0.4 ml of an emulsified liquid agent prepared in the same manner as in Example 1 from a cleaning composition for the intestinal tract (amount of dimethyl polysiloxane added: 0.14, 0.42, 1.4, 4.2, 14 and 42 mg), a commercially available lavage solution for intestinal tract which was the same as that in Test Example 1 (a comparative solution) or water (a control) was placed in a test tube and mixed with 0.4 ml of 1% BSA solution prepared by dissolving bovine serum albumin manufactured by Sigma in a physiological saline solution to an extent of 1 w/v %. Air was introduced at the rate of 3.3 ml/minute for 60 seconds from a polyethylene tube using an infusion pump (manufactured by Nipuro) to generate foam and the height (mm) from the liquid surface to the top end of the foam was measured. The test was repeated 5 times with each solution. The results are shown in FIG. 2. It is apparent from FIG. 2 that the lavage solution according to the present invention significantly reduced foam generation as compared with the comparative group and the control group. In FIG. 2, the plots are average values, the mark ** means "$p<0.01$" as compared with the comparative group and the mark ## means "$p<0.01$" as compared with the control group.

Acute Toxicity Test Example

Each of an emulsified liquid agent prepared in the same manner as in Example 1 from the cleaning composition for the intestinal tract (adding amount of dimethyl polysiloxane:412.37 mg/liter) and a commercially available lavage solution for the intestinal tract which was the same as that in Test Example 1 was orally administered to male SD strain rats (six weeks age) at a dose of 20 ml/kg every 30 minutes for four times. After the administration, the general state of the rats was observed every one hour and, from the next day, once daily for 14 days. In addition, body weight was checked on the day of the administration and on the first, third, seventh and fourteenth days from the administration. Therefor—Each test group consisted of 5 rats. Results of the body weight measurements are given in FIG. 3.

In both groups, a diarrhea symptom was noted in all cases after 3~5 hours from the administration but this symptom recovered on the next day of the administration and, until the 14th day after that, no abnormal observation was noted. The diarrhea symptom which was noted in all of the cases in both groups was due to a pharmacological effect and it is unlikely that there was a toxic action. As is apparent from FIG. 3, there was no significant difference between the body weight therefor gain between the groups. Accordingly, there is no difference in terms of toxicity between the lavage solution prepared in the acute toxicity test example of the present invention and that which is commercially available.

The lavage solution for intestinal tract according to the present invention is capable of significantly reducing foam generation as compared with commercially available products and is extremely useful for observation and measurement of the intestines after cleaning the intestinal tract.

What is claimed is:

1. A lavage solution for intestinal tract which is an emulsified liquid agent consisting of a water-soluble high-molecular weight compound which is at least one compound selected from the group consisting of polyethylene glycol, dextran, dextrin, hydroxyethyl starch, polydextrose, gum arabic, pullulan, pectin and carboxymethyl cellulose, an electrolyte suitable for administration to humans, a silicone containing antifoaming agent, and, as optional components, a sweetener and a perfume.

2. A lavage solution for intestinal tract according to claim 1 wherein the water-soluble high-molecular weight compound is polyethylene glycol.

3. A lavage solution for intestinal tract according to claim 2 wherein the electrolyte is at least one compound selected from the group consisting of sodium sulfate, potassium chloride, sodium chloride and sodium bicarbonate.

4. A lavage solution for intestinal tract according to claim 2 wherein 0.2–400 mg/liter of dimethyl polysiloxane is contained as the antifoaming agent.

5. A lavage solution for intestinal tract according to claim 2 wherein amounts of the water-soluble high-molecular weight compound and ions of the electrolyte are selected from the following compositional ranges:

| Water-soluble high-molecular weight compound | 10–160 g/liter |
|---|---|
| $Na^+$ | 30–150 mEq/liter |
| $K^+$ | 3–20 mEq/liter |
| $Cl^-$ | 20–70 mEq/liter |
| $HCO_3^-$ | 10–30 mEq/liter |
| $SO_4^{2-}$ | 0–100 mEq/liter. |

6. A lavage solution for intestinal tract according to claim 1 wherein the electrolyte is at least one compound selected from the group consisting of sodium sulfate, potassium chloride, sodium chloride and sodium bicarbonate.

7. A lavage solution for intestinal tract according to claim 6 wherein 0.2–400 mg/liter of dimethyl polysiloxane is contained as the antifoaming agent.

8. A lavage solution for intestinal tract according to claim 6 wherein amounts of the water-soluble high-molecular weight compound and ions of the electrolyte are selected from the following compositional ranges:

| Water-soluble high-molecular weight compound | 10–160 g/liter |
|---|---|
| $Na^+$ | 30–150 mEq/liter |
| $K^+$ | 3–20 mEq/liter |
| $Cl^-$ | 20–70 mEq/liter |
| $HCO_3^-$ | 10–30 mEq/liter |
| $SO_4^{2-}$ | 0–100 mEq/liter. |

9. A lavage solution for intestinal tract according to claim 1 wherein 0.2–400 mg/liter of dimethyl polysiloxane is contained as the antifoaming agent.

10. A lavage solution for intestinal tract according to claim 9 wherein amounts of the water-soluble high-molecular weight compound and ions of the electrolyte are selected from the following compositional ranges:

| Water-soluble high-molecular weight compound | 10–160 g/liter |
|---|---|
| $Na^+$ | 30–150 mEq/liter |
| $K^+$ | 3–20 mEq/liter |
| $Cl^-$ | 20–70 mEq/liter |
| $HCO_3^-$ | 10–30 mEq/liter |
| $SO_4^{2-}$ | 0–100 mEq/liter. |

11. A lavage solution for intestinal tract according to claim 1 wherein amounts of the water-soluble high-molecular weight compound and ions of the electrolyte are selected from the following compositional ranges:

| Water-soluble high-molecular weight compound | 10–160 g/liter |
|---|---|
| $Na^+$ | 30–150 mEq/liter |
| $K^+$ | 3–20 mEq/liter |
| $Cl^-$ | 20–70 mEq/liter |
| $HCO_3^-$ | 10–30 mEq/liter |
| $SO_4^{2-}$ | 0–100 mEq/liter. |

12. A method for preparing a lavage solution for intestinal tract which comprises mixing components consisting of a water-soluble high-molecular weight compound which is at least one compound selected from the group consisting of polyethylene glycol, dextran, dextrin, hydroxyethyl starch, polydextrose, gum arabic, pullulan, pectin and carboxymethyl cellulose, an electrolyte suitable for administration to humans, and, as optional components, a sweetener and a perfume, diffusing the mixture with a silicone containing antifoaming agent to prepare a cleaning composition and dissolving the composition into water to emulsify and disperse the composition and form the lavage solution.

13. A method for preparing a lavage solution for intestinal tract which comprises mixing components consisting of a water-soluble high-molecular weight compound which is at least one compound selected from the group consisting of polyethylene glycol, dextran, dextrin, hydroxyethyl starch, polydextrose, gum arabic, pullulan, pectin and carboxymethyl cellulose, an electrolyte suitable for administration to humans, a silicone containing antifoaming agent, and, as optional components, a sweetener and a perfume, to prepare a cleaning composition and dissolving the composition into water to emulsify and disperse the composition and form the lavage solution.

14. A cleaning composition useful for preparing a lavage solution for intestinal tract consisting of a water-soluble high-molecular weight compound which is at least one compound selected from the group consisting of polyethylene glycol, dextran, dextrin, hydroxyethyl starch, polydextrose, gum arabic, pullulan, pectin and carboxymethyl cellulose, an electrolyte suitable for administration to humans, an antifoaming agent of a silicone type, and, as optional components, a sweetener and a perfume.

* * * * *